United States Patent
Carter et al.

(10) Patent No.: US 9,615,913 B2
(45) Date of Patent: Apr. 11, 2017

(54) MATERIALS AND METHODS FOR IMPROVED BONE TENDON BONE TRANSPLANTATION

(71) Applicant: RTI Surgical, Inc., Alachua, FL (US)

(72) Inventors: Kevin C. Carter, Gainesville, FL (US); Michael Esch, Alachua, FL (US); Paul LaRochelle, Satelite Beach, FL (US); James Gross, Alachua, FL (US)

(73) Assignee: RTI Surgical, Inc, Alachua, FL (US)

(*) Notice: Subject to any disclaimer, the term of this patent is extended or adjusted under 35 U.S.C. 154(b) by 0 days.

(21) Appl. No.: 14/669,782

(22) Filed: Mar. 26, 2015

(65) Prior Publication Data

US 2015/0265395 A1    Sep. 24, 2015

Related U.S. Application Data

(63) Continuation of application No. 13/431,459, filed on Mar. 27, 2012, now abandoned, which is a
(Continued)

(51) Int. Cl.
*A61F 2/08* (2006.01)
*A61B 17/16* (2006.01)
(Continued)

(52) U.S. Cl.
CPC ........ *A61F 2/0811* (2013.01); *A61B 17/1635* (2013.01); *A61B 17/1637* (2013.01);
(Continued)

(58) Field of Classification Search
CPC .. A61F 2/0811; A61F 2/08; A61F 2002/0811; A61F 2002/087;
(Continued)

(56) References Cited

U.S. PATENT DOCUMENTS 4,400,833 A    8/1983 Kurland
4,605,414 A    8/1986 Czajka
(Continued)

FOREIGN PATENT DOCUMENTS

FR    2739773    4/1997
JP    A H05-502395    4/1993
(Continued)

OTHER PUBLICATIONS

Frank Noyes et al, Reconstruction of the Anterior Cruciate Ligament with Human Allograft. Comparison of Early and Later Results, JBJS The Journal of Bone & Joint Surgery (3 pages).*
(Continued)

*Primary Examiner* — Alvin Stewart
(74) *Attorney, Agent, or Firm* — McAndrews, Held and Malloy

(57) ABSTRACT

Disclosed herein is an improved Bone Tendon Bone graft for use in orthopedic surgical procedures. Specifically exemplified herein is a Bone Tendon Bone graft comprising one or more bone blocks having a groove cut into the surface thereof, wherein said groove is sufficient to accommodate a fixation screw. Also disclosed is a method of harvesting grafts that has improved efficiency and increases the quantity of extracted tissue and minimizes time required by surgeon for implantation.

15 Claims, 7 Drawing Sheets

Related U.S. Application Data continuation of application No. 10/846,399, filed on May 14, 2004, now Pat. No. 8,167,943, which is a continuation of application No. 09/528,034, filed on Mar. 17, 2000, now Pat. No. 6,805,713, which is a continuation-in-part of application No. 09/481,319, filed on Jan. 11, 2000, now Pat. No. 6,497,726.

(51) Int. Cl.
*A61F 2/28* (2006.01)
*A61F 2/46* (2006.01)

(52) U.S. Cl.
CPC ............ *A61B 17/1675* (2013.01); *A61F 2/08* (2013.01); *A61B 2217/007* (2013.01); *A61F 2002/087* (2013.01); *A61F 2002/0858* (2013.01); *A61F 2002/0882* (2013.01); *A61F 2002/2839* (2013.01); *A61F 2002/4649* (2013.01); *A61F 2230/0069* (2013.01); *A61F 2310/00359* (2013.01)

(58) Field of Classification Search
CPC ...... A61F 2002/0858; A61F 2002/0882; A61F 2002/2839
USPC ......... 623/13.11–13.2, 16.11, 18.11; 606/53, 606/54, 60, 246–249, 62–65, 300, 321, 88
See application file for complete search history.

(56) References Cited

U.S. PATENT DOCUMENTS

| | | |
|---|---|---|
| 4,804,383 A | 2/1989 | Rey et al. |
| 4,870,957 A | 10/1989 | Goble et al. |
| 4,927,421 A | 5/1990 | Goble et al. |
| 4,942,875 A | 7/1990 | Hlavacek et al. |
| 5,004,474 A | 4/1991 | Fronk et al. |
| 5,062,843 A | 11/1991 | Mahony, III |
| 5,067,962 A | 11/1991 | Campbell et al. |
| 5,078,744 A | 1/1992 | Chvapil |
| 5,092,887 A | 3/1992 | Gendler |
| 5,108,431 A | 4/1992 | Mansat et al. |
| 5,139,520 A | 8/1992 | Rosenberg |
| 5,151,104 A | 9/1992 | Kenna |
| 5,152,790 A | 10/1992 | Rosenberg et al. |
| 5,211,647 A | 5/1993 | Schmieding |
| 5,217,495 A | 6/1993 | Kaplan et al. |
| 5,234,430 A | 8/1993 | Huebner |
| 5,263,984 A | 11/1993 | Li et al. |
| 5,282,802 A | 2/1994 | Mahony, III |
| 5,320,115 A | 6/1994 | Kenna |
| 5,366,457 A | 11/1994 | McGuire et al. |
| 5,370,662 A | 12/1994 | Stone et al. |
| 5,383,878 A | 1/1995 | Roger et al. |
| 5,391,169 A | 2/1995 | McGuire |
| 5,393,302 A | 2/1995 | Clark et al. |
| RE34,871 E | 3/1995 | McGuire et al. |
| 5,397,356 A | 3/1995 | Goble et al. |
| 5,397,357 A | 3/1995 | Schmieding et al. |
| 5,425,733 A | 6/1995 | Schmieding |
| 5,425,767 A | 6/1995 | Steininger et al. |
| 5,437,675 A | 8/1995 | Wilson |
| 5,454,811 A | 10/1995 | Huebner |
| 5,496,326 A | 3/1996 | Johnson |
| 5,507,813 A | 4/1996 | Dowd et al. |
| 5,562,669 A | 10/1996 | McGuire |
| 5,562,671 A | 10/1996 | Goble et al. |
| 5,571,184 A | 11/1996 | DeSatnick |
| 5,632,748 A | 5/1997 | Beck, Jr. et al. |
| 5,681,314 A | 10/1997 | Derouin et al. |
| 5,688,285 A | 11/1997 | Yamada |
| 5,733,289 A | 3/1998 | Seedhom et al. |
| 5,766,250 A | 6/1998 | Chervitz et al. |
| 5,772,664 A | 6/1998 | DeSatnick et al. |
| 5,871,504 A | 2/1999 | Eaton et al. |
| 5,897,570 A | 4/1999 | Palleva et al. |
| 5,951,560 A | 9/1999 | Simon et al. |
| 5,961,520 A | 10/1999 | Beck, Jr. et al. |
| 5,984,966 A | 11/1999 | Kiema et al. |
| 5,989,253 A | 11/1999 | Bigliardi |
| 6,001,100 A | 12/1999 | Sherman et al. |
| 6,099,530 A | 8/2000 | Simonian et al. |
| 6,099,568 A | 8/2000 | Simonian et al. |
| 6,190,411 B1 | 2/2001 | Lo |
| 6,200,347 B1 | 3/2001 | Anderson et al. |
| 6,210,440 B1 | 4/2001 | Stone et al. |
| 6,221,107 B1 | 4/2001 | Steiner et al. |
| 6,235,057 B1 | 5/2001 | Roger et al. |
| 6,283,973 B1 | 9/2001 | Hubbard et al. |
| 6,306,168 B1 | 10/2001 | Berrang et al. |
| 6,355,066 B1 | 3/2002 | Kim |
| 6,379,361 B1 | 4/2002 | Beck et al. |
| 6,440,134 B1 | 8/2002 | Zaccherotti et al. |
| 6,458,158 B1 | 10/2002 | Anderson et al. |
| 6,461,373 B2 | 10/2002 | Wyman et al. |
| 6,497,726 B1 | 12/2002 | Carter et al. |
| 6,533,816 B2 | 3/2003 | Sklar |
| 6,579,295 B1 | 6/2003 | Supinski |
| 6,780,187 B2 | 8/2004 | Supinski |
| 6,805,713 B1 | 10/2004 | Carter et al. |
| 6,893,462 B2 | 5/2005 | Buskirk et al. |
| 7,008,451 B2 | 3/2006 | Justin et al. |
| 7,083,647 B1 | 8/2006 | Sklar et al. |
| 7,135,025 B2 | 11/2006 | Pohjonen et al. |
| 7,144,425 B2 | 12/2006 | Steiner et al. |
| 7,172,595 B1 | 2/2007 | Goble |
| 7,182,781 B1 | 2/2007 | Bianchi et al. |
| 7,235,100 B2 | 6/2007 | Martinek |
| 7,309,356 B2 | 12/2007 | Steiner |
| 7,347,872 B2 | 3/2008 | Goulet et al. |
| 7,357,947 B2 | 4/2008 | Nimni |
| 7,513,910 B2 | 4/2009 | Buskirk et al. |
| 7,588,586 B2 | 9/2009 | Whittaker |
| 7,594,929 B2 | 9/2009 | Collette |
| 7,648,524 B2 | 1/2010 | Zhang et al. |
| 7,648,676 B2 | 1/2010 | Mills et al. |
| 7,699,893 B2 | 4/2010 | Donnelly et al. |
| 7,727,278 B2 | 6/2010 | Olsen et al. |
| 7,749,250 B2 | 7/2010 | Stone et al. |
| 7,776,089 B2 | 8/2010 | Bianchi et al. |
| D625,822 S | 10/2010 | Lewis et al. |
| D630,329 S | 1/2011 | Goede et al. |
| 7,879,094 B2 | 2/2011 | Baird et al. |
| 8,167,943 B2 | 5/2012 | Carter et al. |
| 2002/0165611 A1 | 11/2002 | Enzerink et al. |
| 2008/0195115 A1 | 8/2008 | Oren et al. |
| 2009/0234451 A1 | 9/2009 | Manderson |
| 2009/0248068 A1 | 10/2009 | Lombardo et al. |
| 2009/0319043 A1 | 12/2009 | McDevitt et al. |
| 2010/0082103 A1 | 4/2010 | Blunn et al. |
| 2010/0100182 A1 | 4/2010 | Barnes et al. |
| 2010/0121449 A1 | 5/2010 | Sklar et al. |
| 2010/0161054 A1 | 6/2010 | Park et al. |
| 2010/0161055 A1 | 6/2010 | Donnelly et al. |
| 2010/0217389 A1 | 8/2010 | Cheng et al. |
| 2010/0249929 A1 | 9/2010 | Kurz et al. |
| 2010/0249930 A1 | 9/2010 | Myers |
| 2010/0274355 A1 | 10/2010 | McGuire et al. |
| 2010/0312341 A1 | 12/2010 | Kaiser et al. |
| 2012/0083787 A1 | 4/2012 | Oren et al. |

FOREIGN PATENT DOCUMENTS

| | | |
|---|---|---|
| JP | A H09-10245 | 1/1997 |
| JP | A H10-155829 | 6/1998 |
| JP | 10155820 | 8/1998 |
| WO | 98/22047 | 5/1998 |
| WO | 99/21515 | 5/1999 |

OTHER PUBLICATIONS

Noyes et al., Bone-patellar ligament-bone and fascia lata allografts for reconstruction of the anterior cruciate ligament. Journal of Bone and Joint Surgery, 1990; 72A(8); 1125-1136.

(56) References Cited

OTHER PUBLICATIONS

Office Action dated Jan. 23, 2004 for U.S. Appl. No. 10/013,328, Inventor Kevin C. Carter.
Office Action dated Jan. 29, 2007 for U.S. Appl. No. 09/924,110, Inventor Kevin C. Carter.
Office Action dated Mar. 3, 2003 for U.S. Appl. No. 09/528,034, Inventor Kevin C. Carter.
Office Action dated Mar. 18, 2011 for U.S. Appl. No. 11/796,282, Inventor Kevin C. Carter.
Office Action dated Apr. 2, 2008 for U.S. Appl. No. 10/013,328, Inventor Kevin C. Carter.
Office Action dated Apr. 6, 2005 for U.S. Appl. No. 10/013,328, Inventor Kevin C. Carter.
Office Action dated Apr. 17, 2009 for U.S. Appl. No. 11/796,282, Inventor Kevin C. Carter.
Office Action dated Apr. 18, 2005 for U.S. Appl. No. 09/924,110, Inventor Kevin C. Carter.
Office Action dated Apr. 21, 2008 for U.S. Appl. No. 10/846,399, Inventor Kevin C. Carter.
Office Action dated May 2, 2006 for U.S. Appl. No. 09/924,110, Inventor Kevin C. Carter.
Office Action dated May 10, 2011 for U.S. Appl. No. 12/563,830, Inventor Kevin C. Carter.
Office Action dated May 25, 2006 for U.S. Appl. No. 10/013,328, Inventor Kevin C. Carter.
Office Action dated Jun. 13, 2006 for U.S. Appl. No. 10/846,399, Inventor Kevin C. Carter.
Office Action dated Jul. 23, 2007 for U.S. Appl. No. 10/846,399, Inventor Kevin C. Carter.
Office Action dated Aug. 5, 2010 for U.S. Appl. No. 11/796,282, Inventor Kevin C. Carter.
Office Action dated Aug. 8, 2007 for U.S. Appl. No. 10/013,328, Inventor Kevin C. Carter.
Office Action dated Sep. 11, 2002 for U.S. Appl. No. 09/528,034, Inventor Kevin C. Carter.
Office Action dated Sep. 24, 2003 for U.S. Appl. No. 09/924,110, Inventor Kevin C. Carter.
Office Action dated Sep. 28, 2004 for U.S. Appl. No. 09/924,110, Inventor Kevin C. Carter.
Office Action dated Oct. 5, 2005 for U.S. Appl. No. 10/013,328, Inventor Kevin C. Carter.
Office Action dated Oct. 18, 2005 for U.S. Appl. No. 09/924,110, Inventor Kevin C. Carter.
Office Action dated Nov. 18, 2003 for U.S. Appl. No. 09/528,034, Inventor Kevin C. Carter.
Office Action dated Dec. 7, 2001 for U.S. Appl. No. 09/481,319, Inventor Kevin C. Carter.
Office Action dated Dec. 7, 2009 for U.S. Appl. No. 11/796,282, Inventor Kevin C. Carter.
Office Action dated Dec. 18, 2002 for U.S. Appl. No. 09/528,034, Inventor Kevin C. Carter.
Office Action dated Dec. 19, 2008 for U.S. Appl. No. 10/846,399, Inventor Kevin C. Carter.
Requirement for Restriction/Election in U.S. Appl. No. 09/528,034, dated Aug. 22, 2001.
U.S. Patent and Trademark Office, Amendment filed in U.S. Appl. No. 09/528,034, dated Mar. 10, 2004.
U.S. Patent and Trademark Office, Election Response filed in U.S. Appl. No. 10/013,328, dated Jul. 11, 2003.
U.S. Patent and Trademark Office, Response filed in U.S. Appl. No. 09/481,319, dated May 7, 2002.
U.S. Patent and Trademark Office, Response filed in U.S. Appl. No. 09/481,319, dated Oct. 22, 2001.
U.S. Patent and Trademark Office, Response filed in U.S. Appl. No. 09/528,034, dated Feb. 2, 2004.
U.S. Patent and Trademark Office, Response filed in U.S. Appl. No. 09/528,034, dated May 20, 2002.
U.S. Patent and Trademark Office, Response filed in U.S. Appl. No. 09/528,034, dated Sep. 2, 2003.
U.S. Patent and Trademark Office, Response filed in U.S. Appl. No. 09/528,034, dated Oct. 22, 2001.
U.S. Patent and Trademark Office, Response filed in U.S. Appl. No. 09/528,034, dated Nov. 11, 2002.
U.S. Patent and Trademark Office, Response filed in U.S. Appl. No. 09/924,110, dated Apr. 7, 2006.
U.S. Patent and Trademark Office, Response filed in U.S. Appl. No. 09/924,110, dated Feb. 11, 2004.
U.S. Patent and Trademark Office, Response filed in U.S. Appl. No. 09/924,110, dated Mar. 28, 2005.
U.S. Patent and Trademark Office, Response filed in U.S. Appl. No. 09/924,110, dated Jul. 11, 2003.
U.S. Patent and Trademark Office, Response filed in U.S. Appl. No. 09/924,110, dated Aug. 15, 2005.
U.S. Patent and Trademark Office, Response filed in U.S. Appl. No. 09/924,110, dated Nov. 2, 2006.
U.S. Patent and Trademark Office, Response filed in U.S. Appl. No. 09/924,110, dated Nov. 23, 2004.
U.S. Patent and Trademark Office, Response filed in U.S. Appl. No. 10/013,328, dated Feb. 8, 2003.
U.S. Patent and Trademark Office, Response filed in U.S. Appl. No. 10/013,328, dated Mar. 9, 2006.
U.S. Patent and Trademark Office, Response filed in U.S. Appl. No. 10/013,328, dated Mar. 19, 2007.
U.S. Patent and Trademark Office, Response filed in U.S. Appl. No. 10/013,328, dated May 4, 2009.
U.S. Patent and Trademark Office, Response filed in U.S. Appl. No. 10/013,328, dated Jul. 10, 2007.
U.S. Patent and Trademark Office, Response filed in U.S. Appl. No. 10/013,328, dated Jul. 14, 2004.
Advisory Action in U.S. Appl. No. 09/924,110, dated Dec. 14, 2004.
Final Rejection in U.S. Appl. No. 09/924,110, dated Jan. 29, 2007.
Final Rejection in U.S. Appl. No. 09/924,110, dated Oct. 18, 2005.
Final Rejection in U.S. Appl. No. 09/924,110, dated Sep. 28, 2004.
Final Rejection in U.S. Appl. No. 10/013,328, dated Apr. 2, 2008.
Final Rejection in U.S. Appl. No. 10/013,328, dated May 25, 2006.
Non-Final Rejection in U.S. Appl. No. 09/924,110, dated Apr. 18, 2005.
Non-Final Rejection in U.S. Appl. No. 09/924,110, dated May 2, 2006.
Non-Final Rejection in U.S. Appl. No. 09/924,110, dated Sep. 24, 2003.
Non-Final Rejection in U.S. Appl. No. 10/013,228, dated Apr. 6, 2005.
Non-Final Rejection in U.S. Appl. No. 10/013,238, dated May 14, 2003.
Non-Final Rejection in U.S. Appl. No. 10/013,328, dated Aug. 8, 2007.
Non-Final Rejection in U.S. Appl. No. 10/013,328, dated Jan. 23, 2004.
Non-Final Rejection in U.S. Appl. No. 10/013,328, dated Oct. 5, 2005.
Requirement for Restriction/Election in U.S. Appl. No. 09/924,110, dated May 16, 2003.
Requirement for Restriction/Election in U.S. Appl. No. 12/563,830, dated Nov. 11, 2010.
Andres C. Staehelin, "Patellar-Tendon ACL: Operative Technique," pp. 1-10 (1996).
Wagner et al., "Hamstring Tendon Versus Patellar Tendon Anterior Cruciate Ligament Reconstruction Using Biodegradable Interference Fit Fixation," The American Journal of Sports Medicine, pp. 1327-1336.
Andres C. Stahelin MD, "Sysorb Bioresorbable Interference Screws Surgical Technique Products Information," pp. 1-24 (2006).
"Arthrex All-Inside ACL RetroConstruction with Bone-Tendon-Bone Grafts," Surgical Technique, pp. 1-8 (2012).
Non-Final Rejection in U.S. Appl. No. 13/431,459, dated Feb. 21, 2013.
Non-Final Rejection in U.S. Appl. No. 13/431,459, dated Nov. 4, 2013.
Non-Final Rejection in U.S. Appl. No. 13/431,459, dated Jan. 7, 2014.

(56) References Cited

OTHER PUBLICATIONS

Final Rejection in U.S. Appl. No. 13/431,459, dated Sep. 26, 2014.
U.S. Patent and Trademark Office, Response filed in U.S. Appl. No. 10/013,328, dated Aug. 15, 2005.
U.S. Patent and Trademark Office, Response filed in U.S. Appl. No. 10/013,328, dated Oct. 2, 2008.
U.S. Patent and Trademark Office, Response filed in U.S. Appl. No. 10/013,328, dated Dec. 13, 2004.
U.S. Patent and Trademark Office, Response filed in U.S. Appl. No. 11/796,282, dated Jan. 5, 2011.
U.S. Patent and Trademark Office, Response filed in U.S. Appl. No. 11/796,282, dated Apr. 7, 2010.
U.S. Patent and Trademark Office, Response filed in U.S. Appl. No. 11/796,282, dated Jul. 14, 2011.
U.S. Patent and Trademark Office, Response filed in U.S. Appl. No. 11/796,282, dated Aug. 17, 2009.
U.S. Patent and Trademark Office, Response filed in U.S. Appl. No. 12/563,830, dated Jan. 3, 2011.
U.S. Patent and Trademark Office, Response filed in U.S. Appl. No. 12/563,830, dated Mar. 4, 2011.
U.S. Patent and Trademark Office, Response filed in U.S. Appl. No. 12/563,830, dated Aug. 10, 2011.
U.S. Patent and Trademark Office, Supplemental Amendment filed in U.S. Appl. No. 09/481,319, dated Jul. 31, 2002.
U.S. Patent and Trademark Office, Supplemental Election Response filed in U.S. Appl. No. 10/013,328, dated Nov. 10, 2003.
U.S. Patent and Trademark Office, Supplemental Response filed in U.S. Appl. No. 11/796,282, dated Aug. 25, 2011.
Advisory Action in U.S. Appl. No. 09/528,034, dated Feb. 24, 2004.
Advisory Action in U.S. Appl. No. 09/528,034, dated Nov. 26, 2002.
Blevins et al., The effects of donor age and strain rate on the biomechanical properties of bone-patellar tendon-bone allografts. American Journal of Sports Medicine, 1994; 22(3):328-333.
Canadian Intellectual Property Office, Response to Examiner's Report in Canadian Patent Application No. 2,397,071, dated Mar. 8, 2006.
Canadian Patent Office, Office Action, in Canadian Patent Application No. 2,397,071, dated Sep. 12, 2005.
European Patent Office, Communication of a notice of opposition, in European Patent No. 1246585, dated Oct. 2, 2009.
European Patent Office, Communication pursuant to Article 96(2) EPC, in European Patent Application No. 01 902 012.2-2310, dated Mar. 9, 2004.
European Patent Office, Communication pursuant to Article 96(2) EPC, in European Patent Application No. 01 902 012.2-2310, dated Jul. 28, 2005.
European Patent Office, Communication under Rule 71(3) EPC, in European Patent Application No. 01 902 012.2-2310, dated Jun. 23, 2008.
European patent Office, Decision rejecting the opposition, in European Patent No. 1246585, dated Jan. 12, 2012.
European Patent Office, Response in European Patent Application No. 01902012.2, dated Sep. 15, 2004.
European Patent Office, Response in European Patent Application No. 01902012.2, dated Dec. 6, 2005.
European Patent Office, Response in European Patent Application No. 01902012.2, dated Oct. 30, 2006.
European Patent Office, Response in European Patent Application No. 01902012.2, dated May 8, 2007.
European Patent Office, Response in European Patent Application No. 01902012.2, dated Jan. 25, 2008.
European Patent Office, Response in European Patent Application No. 01902012.2, dated Feb. 19, 2008.
European Patent Office, Summons to attend oral proceedings pursuant to Rule 71(1) EPC, in European Patent Application No. 01 902 012.2-2310, dated Nov. 22, 2007.
European Patent Office, Summons to attend oral proceedings pursuant to Rule 115(1) EPC, in European Patent No. 1246585, dated May 13, 2011.

Fahey et al., Bone tunnel enlargement after anterior cruciate ligament replacement, American Journal of Sports Medicine, 1994; 22(3):410-414.
Final Rejection in U.S. Appl. No. 09/528,034, dated Nov. 18, 2003.
Final Rejection in U.S. Appl. No. 09/528,034, dated Sep. 11, 2002.
Final Rejection in U.S. Appl. No. 10/846,399, dated Mar. 16, 2011.
Gill Jennings & Every, Comments in response to notice of opposition, in European Patent No. 1246585, dated May 18, 2010.
Indelicato et al., Clinical comparison of freeze-dried and fresh frozen patellar tendon allografts for anterior cruciate ligament reconstruction of the knee, American Journal of Sports Medicine, 1990; 18(4):335-342.
Indelicato et al., The results of fresh-frozen patellar tendon allografts for chronic anterior cruciate ligament deficiency of the knee, American Journal of Sports Medicine, 1992; 20(2):118-121.
International Preliminary Examination Report for PCT/US01/01008 dated Apr. 15, 2003.
International Search Report for PCT/US01/01008 dated Oct. 18, 2001.
International Search Report for PCT/US02/24972 dated Apr. 21, 2003.
International Search Report for PCT/US02/25018 dated Apr. 23, 2003.
International Search Report in PCT/US02/24972, dated Apr. 24, 2003.
International Search Report in PCT/US02/52018, dated Apr. 23, 2003.
Japanese Patent Office, Appeal Decision, in Japanese Patent Application No. 2001-551423 dated Mar. 19, 2009.
Japanese Patent Office, Decision of Rejection, in Japanese Patent Application No. 2001-551423, dated Jun. 28, 2006.
Japanese Patent Office, Notice of Reason for Rejection, in Japanese patent application No. 2006-279110, dated Apr. 4, 2011.
Japanese Patent Office, Notice of Reasons for Rejection, in Japanese Patent Application No. 2006-279110, dated May 28, 2010.
Japanese Patent Office, Notice of Reasons for Rejection, in Japanese Patent Application No. 2001-551423, dated Jun. 2, 2005.
Japanese Patent Office, Pre-Appeal Examination Report, in Japanese Patent Application No. 2001-551423, dated Feb. 27, 2007.
Japanese Patent Office, Response in Japanese Patent Application No. 2006-279110, dated Nov. 26, 2010.
Japanese Patent Office, Response in Japanese Patent Application No. 2001-551423, dated Dec. 8, 2005.
Japanese Patent Office, Response in Japanese Patent Application No. 2001-551423, dated Oct. 3, 2006.
Japanese Patent Office, Response in Japanese Patent Application No. 2001-551423, dated Nov. 16, 2006.
Japanese Patent Office, Response in Japanese Patent Application No. 2001-551423, dated Oct. 31, 2007.
Lambert, Vascularized patellar tendon graft with rigid internal fixation for anterior cruciate ligament insufficiency, Clinical Orthopaedics and Related Research, 1983; 172:85-89.
Liu et al., Biomechanics of two types of bone-tendon-bone grafts for ACL reconstruction, Journal of bone and joint surgery, 1995; 77B(2):232-235.
Non-Final Rejection in U.S. Appl. No. 09/528,034, dated Dec. 18, 2001.
Non-Final Rejection in U.S. Appl. No. 09/528,034, dated Mar. 3, 2003.
Non-Final Rejection in U.S. Appl. No. 10/013,328, dated Dec. 3, 2008.
Non-Final Rejection in U.S. Appl. No. 10/846,399, dated Jul. 7, 2009.
Non-Final Rejection in U.S. Appl. No. 10/846,399, dated Mar. 10, 2010.
Non-Final Rejection in U.S. Appl. No. 10/846,399, dated Sep. 28, 2010.
Noyes, Frank R., et al., "Reconstruction of the Anterior Cruciate Ligament with Human Allograft", The Journal of Bone and Joint Surgery, Incorporated, vol. 78-A, No. 4, Apr. 1996 (14 pages).

* cited by examiner

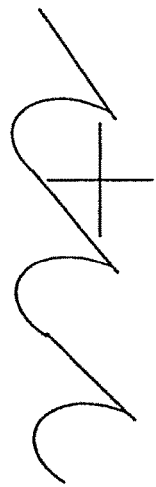
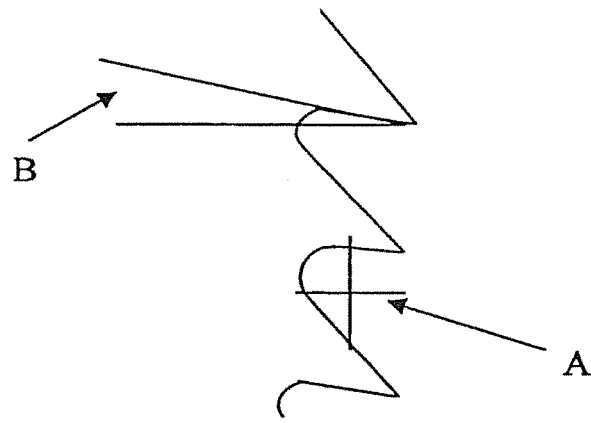
Figure 6A
Figure 6B
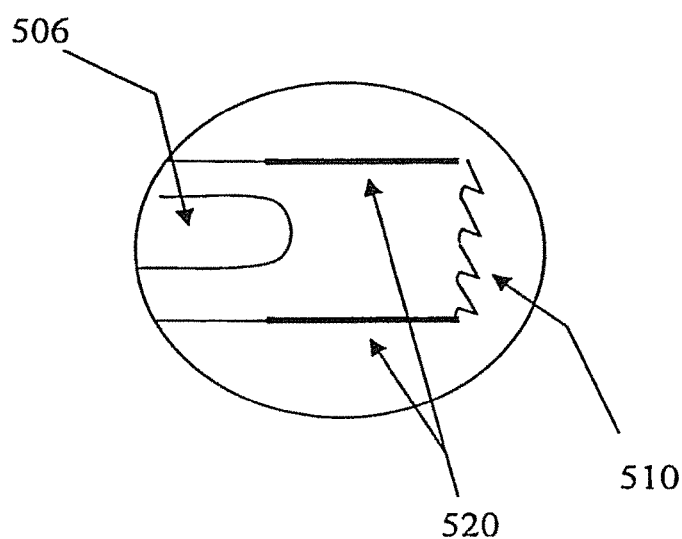
Figure 7

MATERIALS AND METHODS FOR IMPROVED BONE TENDON BONE TRANSPLANTATION

CROSS-REFERENCE TO RELATED APPLICATIONS

The present application is a continuation of U.S. patent application Ser. No. 13/431,459, which was filed on Mar. 27, 2012, which is a continuation of U.S. patent application Ser. No. 10/846,399 (now U.S. Pat. No. 8,167,943), which was filed May 14, 2004, which is a continuation of U.S. patent application Ser. No. 09/528,034 (now U.S. Pat. No. 6,805,713), which was filed Mar. 17, 2000, which is a continuation-in-part of U.S. patent application Ser. No. 09/481,319 (now U.S. Pat. No. 6,497,726), which was filed Jan. 11, 2000. The entire text of the aforementioned applications is incorporated herein by reference in its entirety.

BACKGROUND OF THE INVENTION

Orthopedic medicine is increasingly becoming aware of the vast potential and advantages of using bone/tendon/bone grafts to repair common joint injuries, such as Anterior Cruciate Ligament (ACL) or Posterior Cruciate Ligament (PCL) tears. One technique that is currently used for repairing these types of injuries involves surgically reconnecting the torn portions of a damaged ligament. However, this technique is often not possible, especially when the damage to the ligament is extensive. To address situations where the damage to the joint ligaments is severe, another technique commonly performed involves redirecting tendons to provide increased support to a damaged knee. These conventional techniques are not without their shortcomings; in most cases, the repaired joint lacks flexibility and stability.

The recent utilization of bone/tendon grafts has dramatically improved the results of joint repair in cases of severe trauma. Even in cases of extensive damage to the joint ligaments, orthopedic surgeons have been able to achieve 100 percent range of motion and stability using donor bone/tendon grafts.

Despite these realized advantages, there have been some difficulties encountered with utilizing bone/tendon grafts. For example, surgical procedures involving transplantation and fixation of these grafts can be tedious and lengthy. Currently, bone/tendon/bone grafts must be specifically shaped for the recipient during surgery, which can require thirty minutes to over an hour of time. Further, surgeons must establish a means of attaching the graft, which also takes up valuable surgery time.

Another difficulty associated with using bone/tendon grafts is that there is a limited supply and limited size range available. This can result in a patient having to choose an inferior procedure simply based on the lack of availability of tissue. Accordingly, there is a need in the art for a system that addresses this and the foregoing concerns.

SUMMARY OF THE INVENTION

The subject invention concerns a novel bone tendon bone graft (BTB) that facilitates an easier and more efficient surgery for reconstructing ligaments in a joint. One aspect of the subject invention pertains to a BTB that comprises a tendon and two bone blocks positioned at opposite ends of the tendon, wherein the bone blocks are pre-shaped for uniform and consistent alignment into a recipient bone.

In a specific aspect, the subject invention pertains to a bone tendon bone graft useful in orthopedic surgery comprising one or more bone blocks, and a tendon attached to said one or more bone blocks; wherein said one or more bone blocks is cut to provide a groove sufficient to accommodate a fixation screw. Alternatively, the subject invention pertains to a bone tendon bone graft useful in orthopedic surgery comprising one or more bone blocks and a tendon attached to said one or more bone blocks, wherein said one or more bone blocks is pre-shaped into a dowel.

A further aspect of the subject invention pertains to a method of obtaining a plurality of bone tendon bone grafts comprising excising a first bone plug having attached thereto a tendon or ligament; and excising a second bone plug having attached thereto a tendon or ligament; wherein said first bone plug and said second bone plug are derived from contiguous bone stock and overlap such that excision of said first bone plug or said second bone plug forms a groove in the bone plug that is excised subsequent to the other.

In yet another aspect, the subject invention pertains to a method of conducting orthopedic surgery on a human or an animal comprising obtaining a bone tendon bone graft, said graft comprising a tendon or ligament having two ends, and one or more bone blocks attached to said tendon or ligament, wherein at least one of said one or more bone blocks has a groove suitable for accommodating a fixation screw.

An alternative aspect of the invention pertains to an implant comprising a bone block and a tendon, wherein the bone block comprises a groove for accommodating a fixation screw.

These and other advantageous aspects of the subject invention are described in further detail below.

BRIEF DESCRIPTION OF THE SEVERAL VIEWS OF THE DRAWINGS

FIG. 6A shows a close up view of a teeth configuration that is less desired for use with the subject invention.

FIG. 6B shows a close up view of a preferred embodiment of the teeth of the embodiment shown in FIG. 5.

FIG. 7 is a blown up view of the circled region as shown in FIG. 5.

DETAILED DESCRIPTION OF THE INVENTION

Figure 1:
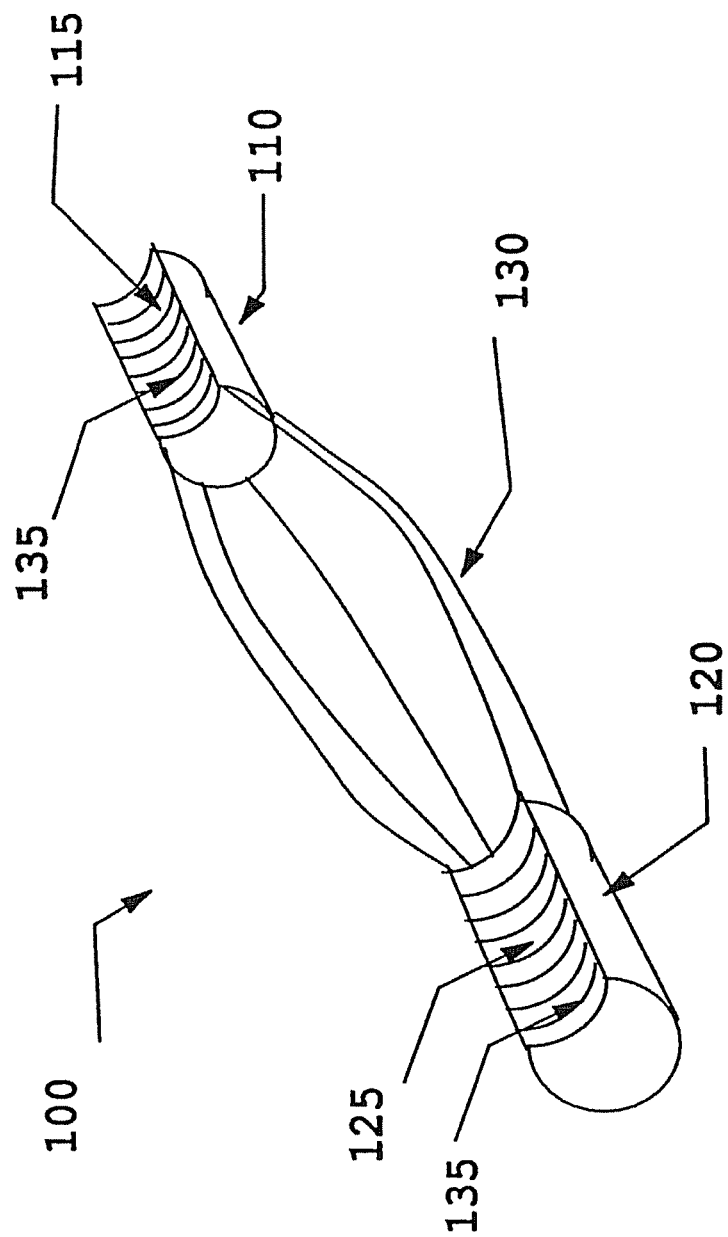
FIG. 1 shows an embodiment of a BTB having a groove with a thread profile disposed thereon.

Referring to FIG. 1, there is shown an embodiment directed to a BTB 100 comprising a first bone block 110 and a second bone block 120 interconnected by a tendon 130, wherein each bone block has been pre-shaped into dowels. The term "tendon" as used herein is intended in its broad sense and refers to fibrous connective tissue for use in grafts, such as, but not limited to, tendons, ligaments and demineralized bone. The terms "BTB" or "bone tendon bone graft" as used herein refer to a graft implant that comprises one or more tendon portions and one or more bone portions. The BTB is preferably isolated from the knee of a donor. However, in view of the teachings herein, those skilled in the art will readily appreciate that other areas of the body are suitable, albeit less preferred, for harvesting BTBs according to the subject invention, such as, but not limited to, the Achilles tendon/calcaneus region or shoulder region. In addition to BTBs having a tendon portion derived from naturally occurring tendon or ligament harvested from a donor, other examples of suitable implants would be readily appreciated by those skilled in the art, such as, but not limited to, segmentally demineralized bone (International Pub. No. WO/99/21515). In a more preferred embodiment, one of the bone blocks is derived from the patella while the other is derived from the end of the tibia, and the tendon is derived from the patellar tendon.

To facilitate placement of a fixation screw, the dowels are preferably machined down the length of the bone block to form radius cuts 115, 125. The radius cuts 115, 125 aid in the attachment of the graft to recipient bone because they provide a groove to position a fixation screw, which results in increased surface area at the contact between the bone block and the screw. The radius cuts 115, 125 provide the additional advantage of increasing the pull out loads of the bone block, as well as filling of "dead" space in the tunnel.

Fixation methods known in the art can be used in accord with the principles of the subject invention, which include, but are not limited to, staples, buttons, screw and washer, interference screws, and self-taping screws. In a preferred embodiment, fixation is accomplished by interference screws and/or self-taping screws. In an even more preferred embodiment, the radius cuts 115, 125 contain a thread profile 135 that matches the thread profile of the fixation screw, thereby further increasing the stability of fixation.

Figure 2A:
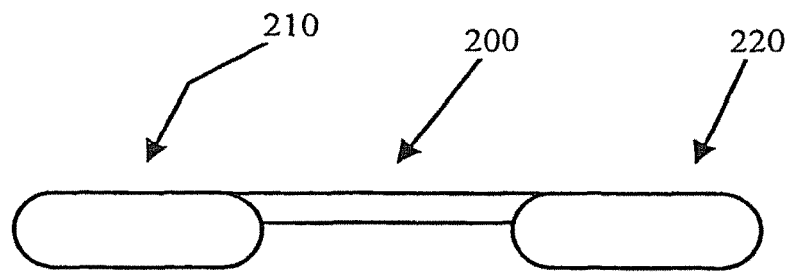
FIG. 2A shows a side view of a first embodiment of a BTB in accordance with the invention.
Figure 2B:
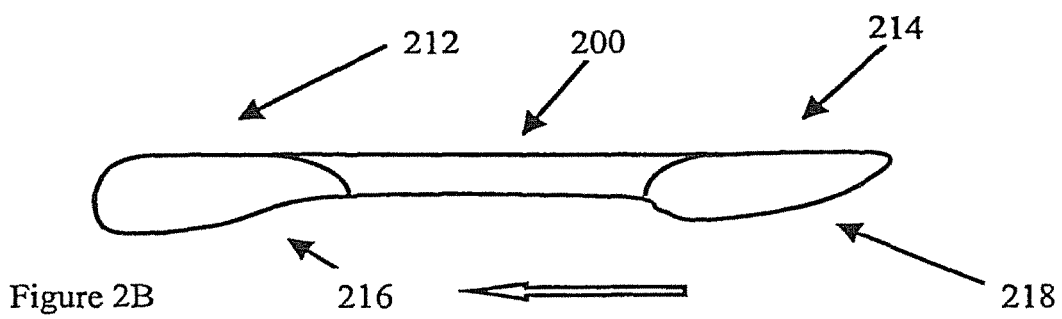
FIG. 2B shows a side view of a second embodiment of a BTB in accordance with the inventions.
Figure 2C:
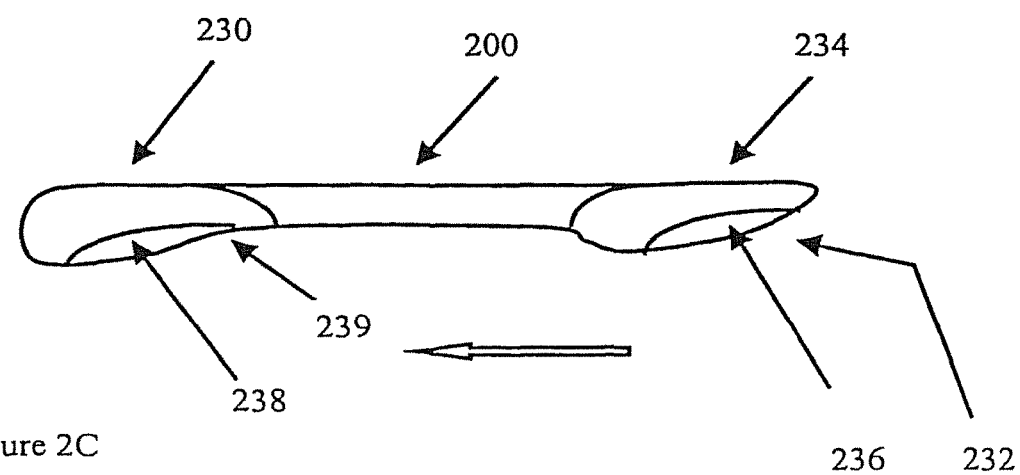
FIG. 2C shows a side view of a third embodiment of a BTB in accordance with the invention.

Referring now to FIG. 2, three different embodiments of the subject BTBs are shown. FIG. 2A shows an embodiment that comprises a basic configuration of the subject BTBs. Bone blocks 210 and 220 are in a pre-shaped dowel form with no groove thereon, and are connected by tendon 100. FIG. 2B shows another version of the BTB, wherein the bone blocks are pre-shaped into dowels with tapered ends. Bone block 212 is a dowel that has a proximal tapered region 216 in relation to tendon 200, and bone block 214 is preshaped into a dowel that has a distal tapered region 218 in relation to tendon 200. FIG. 2C illustrates a preferred version of the invention, which has a bone block 230 with a proximal tapered region 239 and a groove 238 positioned on the bone block 230. This version also comprises a second bone block 234 with a distal tapered region and a groove 236 positioned on bone block 234 as well. The embodiments shown in FIGS. 2B-C are tapered such that implantation into a pre-formed tunnel in recipient to bone is preferred to occur in the direction of the arrow (see also FIG. 4).

Figure 3:
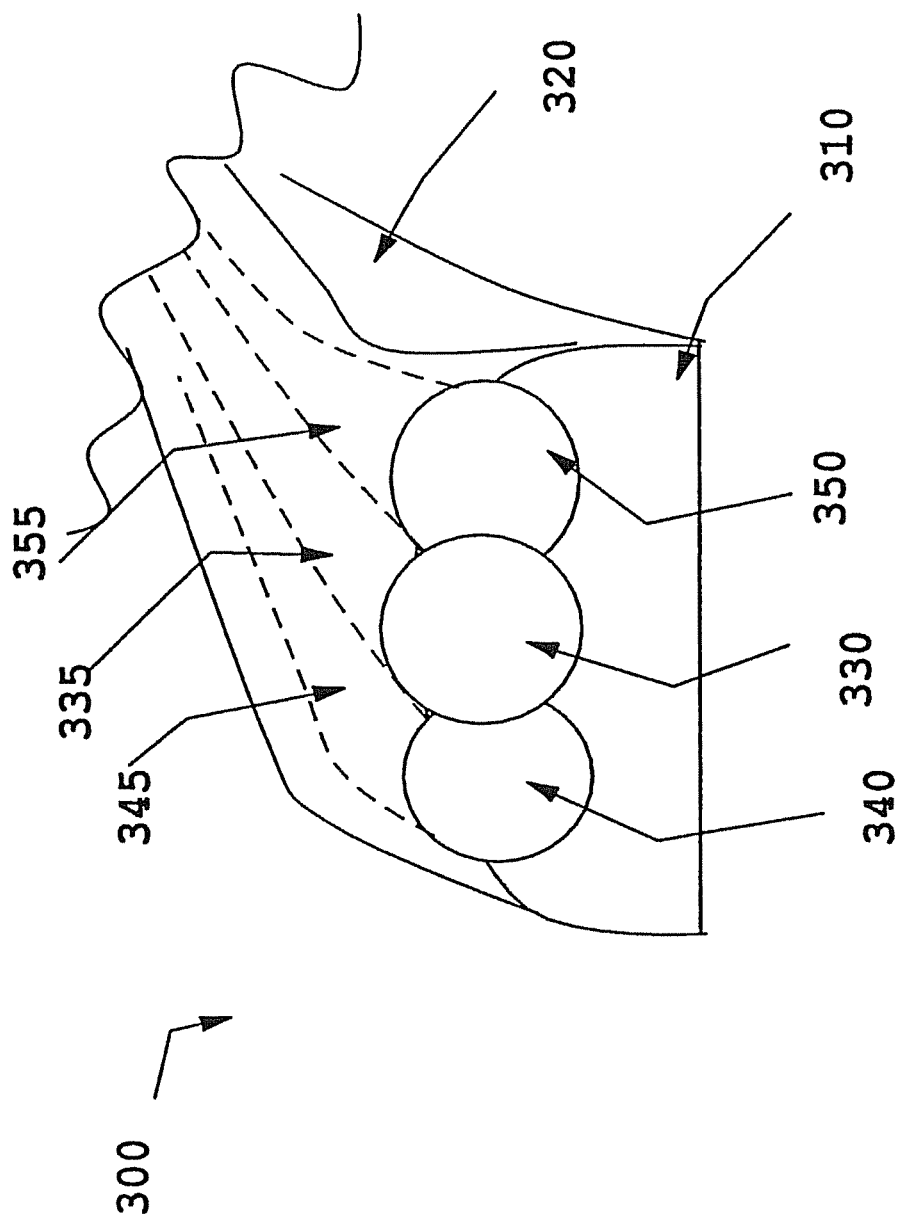
FIG. 3 depicts a frontal view of a donor area for harvesting BTBs in accordance with the teachings herein.

Referring to FIG. 3, an illustration of a donor area 300 is depicted, wherein three separate grafts 335, 345, and 355 are harvested. As shown, the three different grafts individually have at least one bone block 330, 340, and 350. While the sequence of harvesting the grafts is not critical, preferably, graft 335 is excised first, followed by excision of the outside grafts 345, 355. Excising graft 335 first results in the automatic cut in the other donor areas, thereby producing a groove in the bone blocks 340, 350 of the other grafts upon excision. In a preferred embodiment, the donor area is located at the top of the Tibia at the insertion of the patellar tendon 320. In an even more preferred embodiment, the donor area extends the length of the patellar tendon to the patella, wherein bone blocks are excised from the patella.

The bone blocks can be extracted with the use of conventional tools and protocols routinely practiced in the art, such as core cutter and hole saws. In a preferred embodiment, the bone blocks can be extracted through the use of a BTB bone cutter according to the teachings further described below.

The extracted bone blocks 330, 340, and 350 are generally shaped like a plug or dowel and are preferably further shaped by machining through conventional methods known in the art. In a specific embodiment the dowel is machined into dimensions suitable for various surgical procedures. The machining is preferably conducted on a graduated die, a grinding wheel, a lathe, or machining tools may be specifically designed and adapted for this purpose in view of the teachings herein. Preferred dimensions for the dowels include 8 mm, 9 mm, 10 mm, 11 mm, and 12 mm in diameter. Reproducibility of the product dimensions is an important feature for the successful use of such grafts in the clinical setting.

Figure 4:
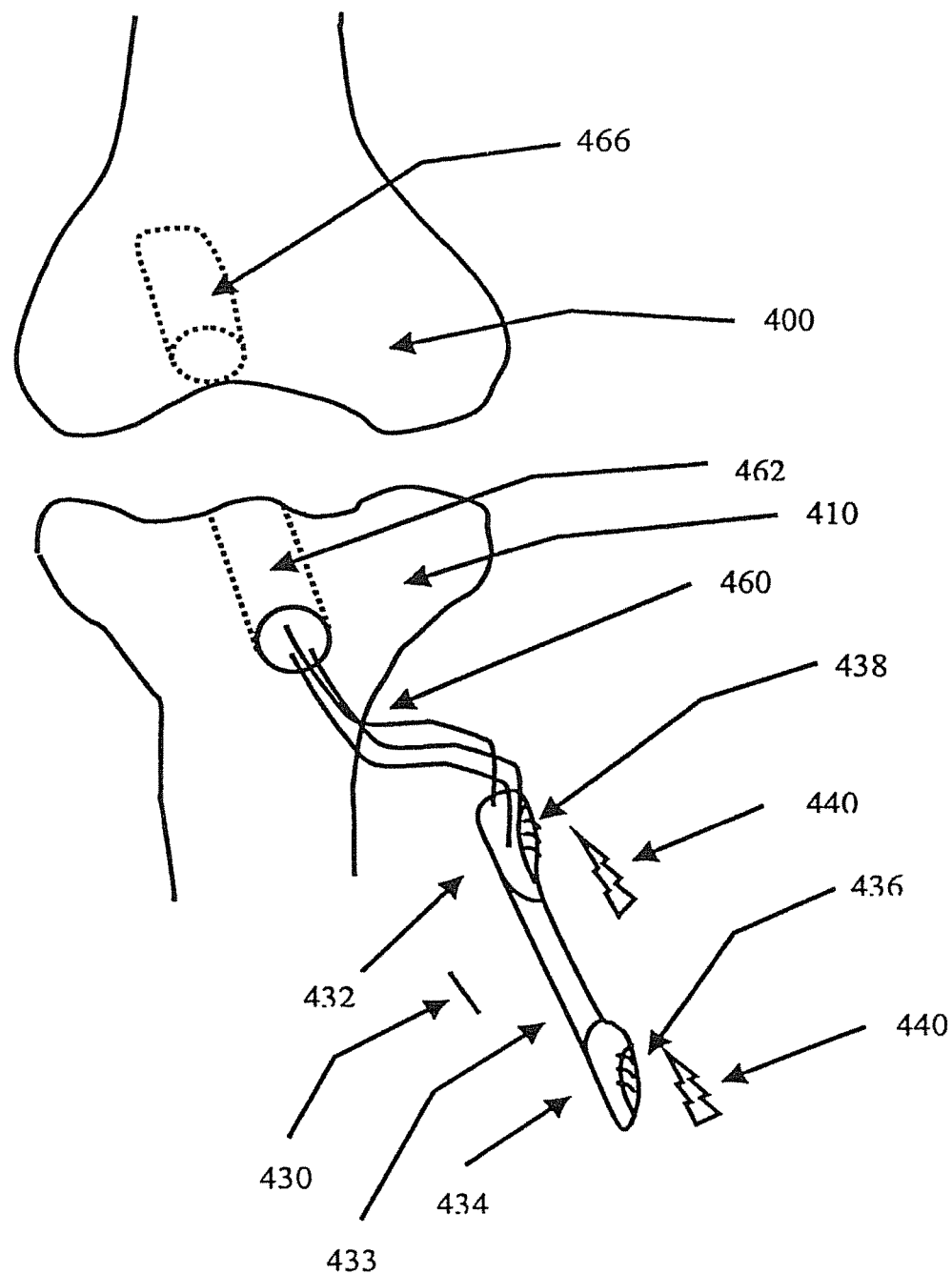
FIG. 4 is a depiction of another embodiment of the invention illustrating a reconstruction of an injured area through implantation of a BTB in accordance with the teachings herein.

In a specific embodiment, the subject invention is directed to a method of repairing an injured cruciate ligament in the knee involving the implantation of a BTB. FIG. 4 illustrates this procedure, and shows a femur 400 and tibia 410 having tunnels formed therein, 466 and 462, respectively, for receiving BTB 430, which comprises two bone blocks 432 and 434 connected by tendon 433. To aid in guiding the BTB 430 through tunnel 462, sutures 460 are optionally engaged to bone block 432, which allow a surgeon to pull the BTB 430 through tunnel 462 where the sutures 460 can then be removed. Once the BTB 430 is properly situated in tunnels 462 and 466, the BTB 430 is secured in the recipient bone by interference screws 440. The interference screws 440 are preferably self taping and are engaged by rotation in the space between grooves 438 and 436 and the inner walls of tunnels 466 and 462, respectively. In an even more preferred embodiment, the BTB can be pre-marked with alignment markings. Such markings can be positioned on the BTB to aid the surgeon in visualizing the depth of the BTB in the tunnels formed for receiving the BTB, as well as visualizing bone ligament junctions and rotation of the BTB.

Figure 5:
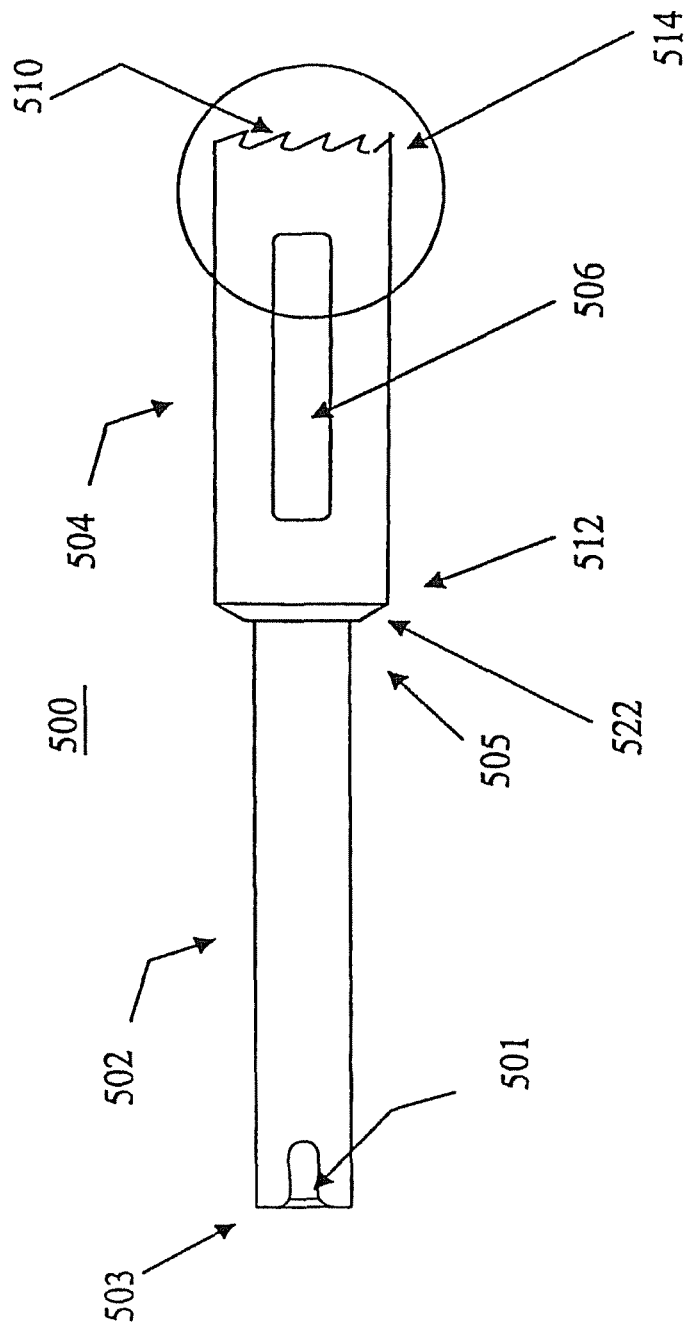
FIG. 5 shows a side view of a BTB core cutter of the subject invention designed for harvesting BTB grafts.

Referring now to FIGS. 5-7, another embodiment of the subject invention is shown that is directed to a BTB harvesting device, such as core cutter 500 that comprises a shaft 502 having a first end 503 and a second end 505. The first end 503 of the shaft 502 preferably has a cavity 501 longitudinally disposed thereon, which is designed for engaging a drill, such as by insertion of a Jacob's chuck attached to a power drill (e.g., Dupuy). The second end 505 of the shaft 502 can be attached to a first end 512 of a hollow cylinder 504. The second end 514 of the cylinder 504 preferably has teeth 510 disposed thereon. In a preferred embodiment the cylinder has at least one slot 506 disposed on its surface to aid in the removal of the cut graft tissue from the core cutter 500. The slot 506 also provides a means to wash the graft during the extraction procedure to thereby decrease the chance of frictional burning of the graft. In a preferred embodiment, the shaft 502 is approximately 90 mm in length, the cylinder 504 is approximately 50 mm in length, and the slot 506 is approximately 30 mm in length.

In an even more preferred embodiment, the first end of the hollow cylinder 512 has a chamfered portion 522 which angles down to the shaft 502.

A blown up view of the core cutter teeth 510 is illustrated in FIG. 6. It is preferred that the radius of the teeth A and rake angle of the teeth B (also referred to as a bottom angle) are of appropriate values as to avoid failure (e.g. bending or breaking) of the teeth, as well as undesired damage to the graft. For example, FIG. 6A shows an unacceptable tooth pattern wherein the radius A and bottom angle B are too large, resulting in insufficient support structure for the tooth and inevitable failure. According to the subject invention, a core cutter having a diameter of approximately 10-11 mm preferably has approximately 14 teeth, with a tooth radius A of approximately 20-30 mm (25 mm being more preferred) and a bottom angle B of approximately 10-20 degrees (15 degrees being more preferred). For core cutters designed for smaller or larger bone blocks, the foregoing dimensions are preferably maintained, while the number of teeth are appropriately decreased or increased. In a preferred embodiment, the number of teeth are decreased or increased by two for every millimeter below or above, respectively, the 10-11 mm cylinder diameter. For example, a core cutter having a 12 mm cylinder diameter would preferably have about 16 teeth.

A blown up view of an end section (circle shown in FIG. 5) of the cylinder 504, is shown in FIG. 7, which illustrates a preferred embodiment of the cylinder 504 wherein the internal diameter (ID) is decreased slightly by adding a relief thickness 520 to the inner surface of the cylinder 504. This embodiment provides an additional convenience when using a size gauging device (e.g. ring) for selecting extracted bone blocks that are within desired parameters. For example, the selection of a BTB through a 10 mm sized gauging device would preferably require the BTB to be a slight fraction smaller in diameter than the gauging device, otherwise any insignificant irregularity in the shape of the BTB might cause it to fail to pass through the gauging device. The relief thickness 520 decreases the ID of the cylinder 504, thereby effectuating this slight modification to the BTB.

Figure 8:
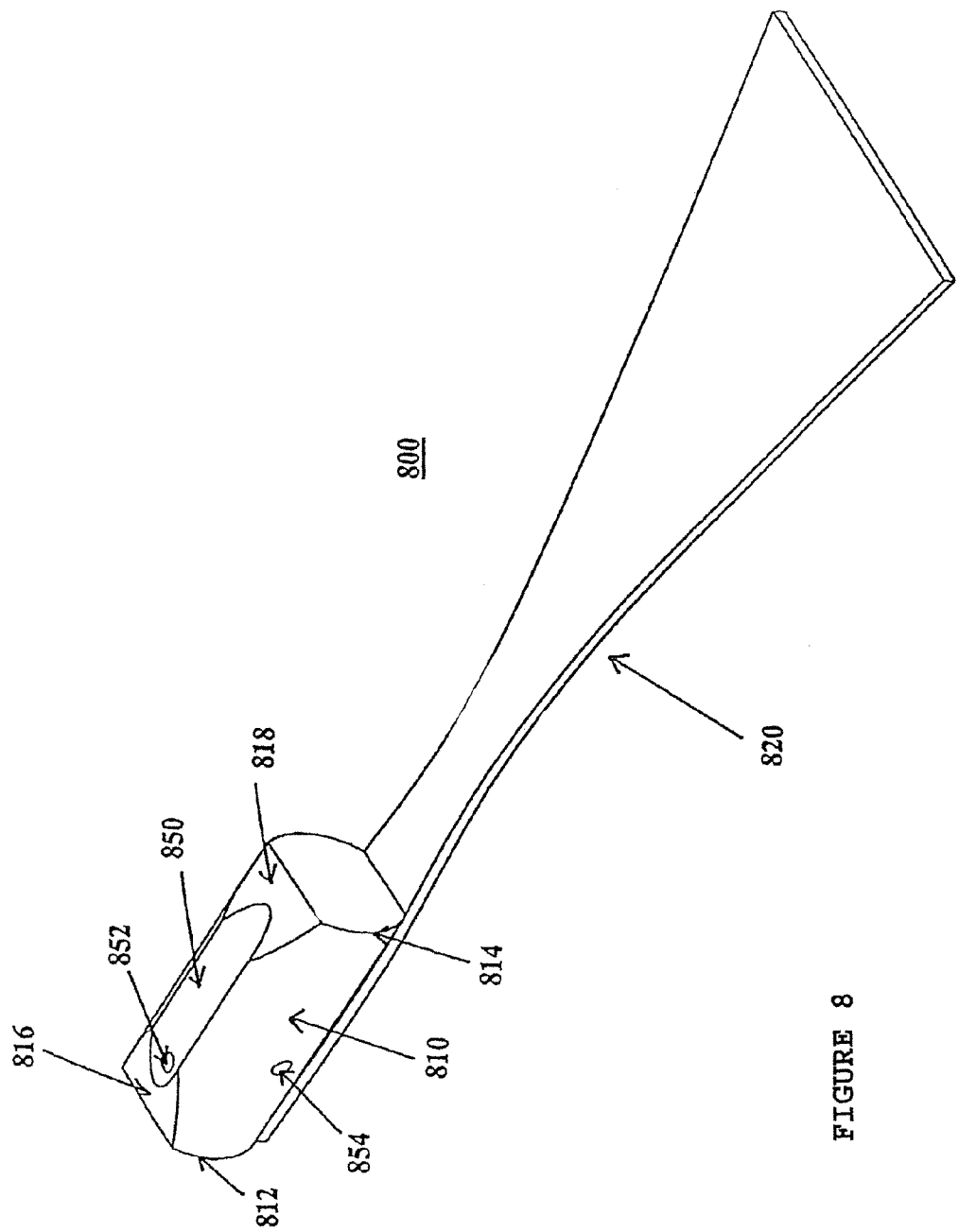
FIG. 8 is three dimensional side view of a further embodiment of the subject BTB that comprises one block that is tapered on both ends.

Shown in FIG. 8 is a further embodiment 800 of the subject BTB that is especially adapted for implantation during knee surgery, wherein the implantation and securement of the BTB is bi-directional. BTB embodiment 800 comprises one bone block portion 810 and one tendon portion 820. A preferred area from which embodiment 800 is harvested would be the heel, thigh, or shoulder. More preferably, the area from which embodiment 800 is harvested is the heel or thigh, whereby tendon portion 820 is derived from an Achilles tendon or quadriceps tendon of a donor. The bone block portion 810 comprises two ends 812 and 814 which both comprise a tapered region 816 and 818, respectively. The presence of the two tapered regions 812 and 814 allows for the BTB embodiment 800 to be inserted and secured bi-directionally, which means, for example, implantation in either the tibial 462 or femoral 466 tunnels as discussed above in reference to the method diagrammed in FIG. 4. Of course, the site of implantation could be approached from a superior point of entry, i.e., establishing a through-tunnel in the femur as opposed to the tibia; BTB embodiment 800 would be suitable for securement in either tunnels in such alternative procedure as well. Further, the bone block 810 can be provided with a groove 850 to aid in the securement of the implant. In addition, during implantation, it may be desirable to have a means for manipulating the implant, such as by sutures or graft insertion tools. Accordingly, BTB embodiment 800 is provided with preformed graft manipulation holes 852 and 854 for receiving a suture and/or graft insertion tools. By way of example of illustrating the orientation of the graft manipulation holes, holes 852 and 854 are shown as being vertical or horizontal, respectively, to the axis of the bone block 810. The preformed graft manipulation holes can be made by conventional methods, such as by drilling. Appropriate tools for insertion into preformed holes 852 and 854 will easily be appreciated by those skilled in the art. Preferably, the graft insertion tool(s) used comprise an end having a shape and size suitable for insertion into the graft manipulation holes.

Those skilled in the art will appreciate that the graft may be an autograft, allograft, or xenograft. Xenograft implants may further require treatments to minimize the level of antigenic agents and/or potentially pathogenic agents present in the graft. Techniques now known, or those which are later developed, for preparing tissue such that it is suitable for and not rejected by the recipient are incorporated herein. In cases where the graft is an allograft or xenograft, a donor is preferably screened for a wide variety of communicable diseases and pathogens, including human immunodeficiency virus, cytomegalovirus hepatitis B, hepatitis C and several other pathogens. These tests may be conducted by any of a number of means conventional in the art, including, but not limited to, ELISA assays, PCR assays, or hemagglutination. Such testing follows the requirements of the following associations: (a) American Association of Tissue Banks. Technical Manual for Tissue Banking, Technical Manual-Musculoskeletal Tissues, pages M19-M20; (b) The Food and Drug Administration, Interim Rule, Federal Register, Vol. 58, No. 238, Tuesday, December 14, Rules and Regulations, 65517, D. Infectious Disease Testing and Donor Screening; (c) MMWR, Vol. 43, No. RR-8, Guidelines for Preventing Transmission of Human Immunodeficiency Virus Through Transplantation of Human Tissue and Organs, pages 4-7; (d) Florida Administrative Weekly, Vol. 10, No. 34, Aug. 21, 1992, 59A-1.001-014, 59A-1.005(12) (c), F.A.C., (12)(a)-(h), 59A-1.005(15, F.A.C., (4) (a)-(8). In addition to a battery of standard biochemical assays, the donor, or their next of kin can be interviewed to ascertain whether the donor engaged in any of a number of high risk behaviors such as having multiple sexual partners, suffering from hemophilia, engaging in intravenous drug use etc. Once a donor has been ascertained to be acceptable, the tissue for obtention of the BTBs as described above are recovered and cleaned.

The teachings of all patents and publications cited throughout this specification are incorporated by reference in their entirety to the extent not inconsistent with the teachings herein.

It should be understood that the examples and embodiments described herein are for illustrative purposes only and that various modifications or changes in light thereof will be suggested to persons skilled in the art and are to be included within the spirit and purview of this application and the scope of the appended claims.

EXAMPLE 1

Procedure for Harvesting of Crude BTB for Patellar Tendon Tibial Donor

A BTB was harvested according to the following procedure:

1. Using blunt and sharp dissection remove the three layers of connective tissue from the anterior portion of the tendon.

2. Using scalpel or scissors cut along the medial and lateral borders of the tendon. Use the scissors to bluntly dissect under the tendon to separate it from the fat layer.

3. Cut around the Patellar block to separate it form the proximal tibia and distal femur. Leave approximately 4 cm of quadriceps tendon attached to the patellar if required. If no quadriceps tendon attachment is specified then remove quadriceps from patellar completely using sharp dissection.

4. Pull tendon away from capsule and remove all excess adipose tissue to the point of tibial insertion.

5. With a saw make a transverse cut through approximately the tibial tuberosity about 30 mm from the tendon insertion point. Make a similar cut about 5 mm proximal to the insertion point, which will remove the tibial plateau.

6. With a saw, cut and square the sides of the tibia bone block even with the tendon.

7. With a saw cut and square the patella block on three sides (if quadriceps tendon is still attached square off only the medial and lateral sides).

8. Remove all extraneous soft tissue and cartilage from the patella, tibial tuberosity and tendon.

9. To hemisect the patellar tendon use a scalpel to divide the tendon into a medial half and a lateral half. Each half should be 14 mm or greater unless otherwise specified.

10. Using a saw, split the patella block and the tibia block in half following the same medial/lateral line used to split the tendon.

11. Thoroughly lavage the bone blocks with sterile water or saline.

EXAMPLE 2

Procedure for Forming Patellar Tendons with Preshaped Dowels for Patellar Tendon Tibial Donor A BTB was harvested according to the following procedure:

1. Using blunt and sharp dissection remove the three layers of connective tissue from the anterior portion of the tendon.

2. Using a scalpel or scissors cut along the medial and lateral borders of the tendon to separate it from the fat layer.

3. Cut around the Patellar block to separate it from the proximal tibia and distal femur.

4. Pull tendon away from capsule and remove all excess adipose tissue to the point of tibial insertion.

5. With a saw make a transverse cut through the tibial tuberosity about 30 mm from the tendon insertion point. Make a similar cut just proximal to the insertion point removing the tibial plateau. Make another cut across the coronal plane 20-30 mm posterior from the insertion point.

6. With a saw square the sides of the tibia bone block.

7. With a saw cut and square the patella block on the three sides.

8. Attach a vice to the tabletop. Place the tibia bone block in the vice so that it holds it along the proximal and distal sides. The distal side of the bone block should be facing the processor with the tendon going away from them. Tighten the vice so that it holds the bone securely but does not crush it.

9. Attach a Jacob's chuck to a drill and insert the appropriate size cutter. Tighten the chuck with the chuck key. Note: At least two plugs should be cut from each bone block.

10. Position the cutter against the bone block so the teeth of the cutter will skim just over the top of the tendon without catching the tendon. Position the cutter so that the maximum attachment is obtained throughout the length of the bone plug.

11. Turn drill on and begin drilling the plug. When the cutter nears the end of the plug, slow the drill until the cutter just breaks through the proximal end of the bone block. Remove the plug from the cutter and drill without damaging the tendon.

12. Repeat steps 10 and 11 for the second plug.

13. Using scissors or a scalpel hemisect the tendon into medial and lateral halves.

14. Remove the excess bone from the table vice and place the patella bone block into the vice so that it holds it along the medial and lateral sides of the block. The proximal side of the patella should be facing the processor with the tendon going away from them. Tighten the vice so that it holds the bone block securely but does not crush it.

15. Repeat steps 10 and 11 for both plugs.

16. When the plugs are completed, remove the excess patella bone from the vice and detach the vice from the table.

17. Remove the cutter from the Jacob's chuck and place a 1.5 mm drill bit into the chuck. Tighten with the chuck key.

18. Using a saw, cut each plug to approximately 30 mm in length (no less than 45 25 mm)

19. Using the Arthrex clamp, place the plug into it with the end of the plug flush with the end of the clamp. Position the plug in the anterior/posterior position. Using the first guide hole nearest the flush end of the plug, drill a hole through the plug with the 1.5 mm drill bit. Turn the plug 180 degrees so that it is positioned in the medial/lateral position. Use the second guide hole from the flush end of the plug to drill a second hole through the plug.

20. Repeat step 19 for all bone plugs.

21. Using a sizing apparatus insert each bone plug into the appropriate size gauge. The entire BTB should slide completely through easily. Trim if necessary.

22. Thoroughly lavage bone plugs with sterile water or saline.

We claim:

1. A recovered and cleaned pre-shaped human allograft implant comprising:
   at least one bone block adapted before surgery for fixation in a bone tunnel having a tunnel diameter;
   said bone block pre-shaped before surgery as a pre-shaped dowel bone block having a dowel diameter specially adapted for fixation in a bone tunnel having said tunnel diameter;
   and
   a natural insertion of a first human tendon into said first human bone block,
   wherein said natural insertion occurs between one of the following bone-tendon pairs,
   a. patellar bone and patellar tendon,
   b. patellar bone and quadriceps tendon,
   c. tibial bone and patellar tendon, or
   d. calcaneus bone and Achilles tendon;
   and wherein said first human tendon runs along at least a portion of the length of said first human bone block and said first human tendon forms at least a portion of an outer surface of said first human bone block; wherein the portion of the outer surface maintains essentially the same contour as the rest of said first human bone block; and
   further wherein said human allograft implant has been treated to minimize the level of antigenic agents and/or potentially pathogenic agents present in the graft.

2. The pre-shaped human allograft implant of claim 1, wherein said first human bone block comprises a human calcaneal bone block in a pre-shaped dowel form with no groove thereon and wherein said natural insertion comprises a natural insertion of the human Achilles tendon into said human calcaneal bone block, and wherein said first human tendon comprises a human Achilles tendon portion derived from a naturally occurring human Achilles tendon.

3. The pre-shaped human allograft implant of claim 1, wherein said first human bone block comprises a human tibial bone block in a pre-shaped dowel form with no groove thereon and wherein said natural insertion comprises a natural insertion of the human patellar tendon into said human tibial bone block, and wherein said first human tendon comprises a human patellar tendon portion derived from a naturally occurring human patellar tendon, said human patellar tendon portion further naturally attached to a human patellar bone block.

4. The pre-shaped human allograft implant of claim 1, wherein said patellar tendon, or said quadriceps tendon or said Achilles tendon is hemisected.

5. The pre-shaped human allograft implant of claim 4, wherein said bone block has at least one side that is cut substantially even with the tendon.

6. The pre-shaped human allograft implant of claim 1, wherein said first human bone block is a pre-shaped cylindrical dowel form with no groove thereon.

7. The pre-shaped human allograft implant of claim 1, wherein said first human bone block is tapered.

8. The pre-shaped human allograft implant of claim 1, wherein said first human bone block is not tapered.

9. A recovered and cleaned pre-shaped human allograft implant comprising:
   a human tibial bone block in a pre-shaped dowel,
   a human patellar tendon portion and
   a human patellar bone block in a pre-shaped dowel;
   wherein said human patellar tendon portion is naturally attached to said human tibial bone block and said human patellar bone block,
   wherein said human tibial bone block is pre-shaped before surgery as a first pre-shaped dowel bone block having a dowel diameter specially adapted for fixation in a bone tunnel having a tunnel diameter and said human patellar bone block is pre-shaped before surgery as a second pre-shaped dowel bone block having a dowel diameter specially adapted for fixation in a bone tunnel having a tunnel diameter;
   and wherein said human patellar tendon portion runs along at least a portion of the length of at least one of said pre-shaped dowels and said human patellar tendon portion forms at least a portion of an outer surface of at least one of said pre-shaped dowels and the portion of the outer surface maintains essentially the same contour as the rest of at least one of said pre-shaped dowels; and
   further wherein said human allograft implant has been treated to minimize the level of antigenic agents and/or potentially pathogenic agents present in the graft.

10. The pre-shaped human allograft implant of claim 9, wherein said human tibial bone block is in a pre-shaped cylindrical dowel form with no groove thereon.

11. The pre-shaped human allograft implant of claim 10, wherein said human patellar bone block is in a pre-shaped cylindrical dowel form with no groove thereon.

12. A recovered and cleaned pre-shaped human allograft implant wherein at least one bone block of said allograft is adapted before surgery for fixation in a bone tunnel having a tunnel diameter, comprising:
   an allograft Achilles tendon naturally attached to a portion of calcaneal bone,
   a natural insertion site of said allograft Achilles tendon, and
   a portion of calcaneal bone distal to said natural insertion site; and
   wherein said allograft Achilles tendon has a medial/lateral division, and at least one side of said portion of calcaneal bone is cut even with said division of said tendon; and
   wherein said tendon runs along at least a portion of the length of said portion of calcaneal bone and said tendon forms at least a portion of an outer surface that maintains essentially the same contour as the rest of the portion of the calcaneal bone; and
   wherein said portion of calcaneal bone is pre-shaped before surgery as a pre-shaped dowel bone block having a dowel diameter specially adapted for fixation in a bone tunnel having a tunnel diameter;
   further wherein said human allograft implant has been treated to minimize the level of antigenic agents and/or potentially pathogenic agents present in the graft.

13. The pre-shaped human allograft implant of claim 12, wherein said portion of calcaneal bone is in a pre-shaped cylindrical dowel form with no groove thereon.

14. The pre-shaped human allograft implant of claim 12, wherein said portion of calcaneal bone is in a pre-shaped cylindrical dowel form and is tapered.

15. The pre-shaped human allograft implant of claim 12, wherein said portion of calcaneal bone is in a pre-shaped cylindrical dowel form and is not tapered.

* * * * *